US009929483B2

(12) United States Patent
Wieters et al.

(10) Patent No.: US 9,929,483 B2
(45) Date of Patent: Mar. 27, 2018

(54) ELECTRICAL CONNECTION PIECE FOR AN ENDOSCOPE AND METHOD FOR ESTABLISHING AN ELECTRICAL CONNECTION IN AN ENDOSCOPE

(71) Applicant: OLYMPUS WINTER & IBE GMBH, Hamburg (DE)

(72) Inventors: Martin Wieters, Barsbuettel (DE); Jens Schnitger, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 15/705,472

(22) Filed: Sep. 15, 2017

(65) Prior Publication Data
US 2018/0006389 A1    Jan. 4, 2018

Related U.S. Application Data

(63) Continuation of application No. PCT/EP2016/054503, filed on Mar. 3, 2016.

(30) Foreign Application Priority Data

Mar. 18, 2015 (DE) .................. 10 2015 204 884

(51) Int. Cl.
H01R 12/00 (2006.01)
H01R 12/59 (2011.01)
(Continued)

(52) U.S. Cl.
CPC ........... *H01R 12/592* (2013.01); *H01R 12/67* (2013.01); *H01R 12/777* (2013.01);
(Continued)

(58) Field of Classification Search
CPC .............................. H01R 12/59; H01R 13/22
See application file for complete search history.

(56) References Cited

U.S. PATENT DOCUMENTS 8,075,477 B2 * 12/2011 Nakamura ........... A61B 1/0011
439/67
8,221,134 B2 * 7/2012 Dove ..................... H01R 13/22
439/493
(Continued)

FOREIGN PATENT DOCUMENTS

DE    102012202133 A1    8/2013
EP        2677736 A1    12/2013
(Continued)

OTHER PUBLICATIONS

International Search Report dated May 13, 2016 issued in PCT/EP2016/054503.

*Primary Examiner* — Tho D Ta
(74) *Attorney, Agent, or Firm* — Scully, Scott, Murphy & Presser, P.C.

(57) ABSTRACT

An electrical connection piece including: a flexible circuit board having: a central section penetrated by contact openings arranged mirror-symmetrically; a first and second arm, each of the first and second arms extending in different directions away from the central section, the end of the first arm having a first end surface, the end of the second arm having a second end surface, the end of the first arm having a third end surface opposing the first end surface and end of the second arm having a fourth end surface opposing the second end surface; first strip conductors extending between the contact openings and first electrical contacting surfaces; and second strip conductors extending between the contact openings and second electrical contacting surfaces; wherein the first electrical contacting surfaces have a contact configuration different from a contact configuration of the second electrical contacting surfaces.

20 Claims, 2 Drawing Sheets

(51) Int. Cl.
*H01R 12/67* (2011.01)
*H01R 13/52* (2006.01)
*H01R 12/77* (2011.01)
*A61B 1/00* (2006.01)
*H01R 13/22* (2006.01)

(52) U.S. Cl.
CPC ...... *H01R 13/5224* (2013.01); *A61B 1/00114* (2013.01); *H01R 12/59* (2013.01); *H01R 13/22* (2013.01); *H01R 2201/12* (2013.01)

(56) References Cited

U.S. PATENT DOCUMENTS

| | | | |
|---|---|---|---|
| 8,622,753 B2 * | 1/2014 | Balzano | H01R 13/22 439/225 |
| 8,668,503 B2 * | 3/2014 | Williams | H01R 12/716 439/369 |
| 8,698,887 B2 | 4/2014 | Makino et al. | |
| 2011/0249106 A1 | 10/2011 | Makino et al. | |
| 2014/0371530 A1 * | 12/2014 | Wieters | A61B 1/0011 600/109 |
| 2015/0228678 A1 | 8/2015 | Yoshida et al. | |

FOREIGN PATENT DOCUMENTS

| | | | |
|---|---|---|---|
| JP | 2000-333903 A | 12/2000 | |
| JP | 2011-217887 A | 11/2011 | |
| WO | WO 2014/065099 A1 | 5/2014 | |
| WO | WO 2014/125070 A1 | 8/2014 | |

\* cited by examiner

ELECTRICAL CONNECTION PIECE FOR AN ENDOSCOPE AND METHOD FOR ESTABLISHING AN ELECTRICAL CONNECTION IN AN ENDOSCOPE

CROSS-REFERENCE TO RELATED APPLICATION

The present application is a continuation of PCT/EP2016/054503 filed on Mar. 3, 2016, which is based upon and claims the benefit to DE 10 2015 204 884.5 filed on Mar. 18, 2015, the entire contents of each of which are incorporated herein by reference.

BACKGROUND

Field

The present application relates to an endoscope, and in particular, to an electrical connection piece for an endoscope comprising an at least partially flexible circuit board having a central section which is penetrated by contact openings for contact pins of a hermetically sealed feedthrough of an image-producing unit of the endoscope, wherein the circuit board further comprises a bendable first arm and a bendable second arm which branch off in different directions from the central section, wherein the first arm at its end facing away from the central section comprises a first flat end surface and the second arm at its end facing away from the central section comprises a second flat end surface, wherein strip conductors extend between the contact openings and first electrical contacting surfaces present in the end surfaces. Moreover, the present application relates to an endoscope comprising a shaft and a hermetically sealed image-producing unit arranged in the shaft. The present application further relates to a method for establishing an electrical connection in an endoscope.

Prior Art

In endoscopes, for example video endoscopes, optics are located at the distal tip of an endoscope shaft, for example an objective lens for viewing straight ahead or for viewing sideways. An image sensor adjoins this objective lens, the image sensor converting the received light into electrical signals which are conducted via suitable electrical conductors to the proximal end. The electrical conductors, by which the signals are transmitted in the interior of the endoscope shaft, may be cables comprising a plurality of shielded or unshielded stranded wires, flexible circuit boards, or the like.

In some endoscopes, both the optics and the image sensor are located in a hermetically sealed chamber. Such an endoscope is disclosed, for example, in DE 10 2012 202 133 A1. Generally, an optical subassembly on the distal tip of the endoscope is also denoted as the "R-unit". It contains the optical lens systems and optionally an optical surface sensor, for example a CCD or CMOS sensor. For contacting such an R-unit, a hermetically sealed plated through-hole of the electrical conductors is present. Such a hermetically sealed electrical feedthrough is implemented, for example, by metal pins and/or contact pins being cast into a glass support. The electrical conductors used for the signal transmission are, for example, directly soldered onto these metal pins.

SUMMARY

It is an object to provide an electrical connection piece for an endoscope, an endoscope and a method for establishing an electrical connection in an endoscope which is flexible in terms of the contacting.

Such object can be solved by an electrical connection piece for an endoscope, comprising an at least partially flexible circuit board having a central section which is penetrated by contact openings for contact pins of a hermetically sealed feedthrough of an image-producing unit of the endoscope, wherein the circuit board further comprises a bendable first arm and a bendable second arm which branch off in different directions from the central section, wherein the first arm at its end facing away from the central section comprises a first flat end surface and the second arm at its end facing away from the central section comprises a second flat end surface, wherein strip conductors extend between the contact openings and first electrical contacting surfaces present in the end surfaces, wherein a contact assignment, which is mirror symmetrical relative to an axis of symmetry, is provided for the contact openings, and also the first arm comprises a flat third end surface opposing the first end surface and the second arm comprises a flat fourth end surface opposing the second end surface, wherein further strip conductors extend between the contact openings and the second electrical contacting surfaces present in the third and fourth end surfaces and wherein the first electrical contacting surfaces are configured for contacting using a first contact technology and/or contact assignment and the second electrical contacting surfaces are configured for contacting using a different second contact technology and/or contact assignment.

Within the context of the present description, "opposing end surfaces" are surfaces which are arranged on opposing flat sides of the respective arm. In particular, the opposing end surfaces are configured and/or arranged to be at least approximately congruent to one another in a direction perpendicular to their surface. The endoscope can be a video endoscope. The image-producing unit can be a video unit or an R-unit. The electrical connection piece can be configured and/or able to be used for a video endoscope with a hermetically sealed video unit which is located in a shaft of the video endoscope.

The electrical connection piece can permit a flexible contact and/or contact assignment of the contacting surfaces, which means that the contact technology and/or contact assignment used therefore does not have to be established in advance. Only at the time when the electrical connection piece is connected to the image-producing unit of the endoscope does a corresponding choice have to be made. The electrical connection piece is, therefore, suitable for different types of connection, wherein a single circuit board design and/or a single electrical connection piece can be used in a plurality of different types of endoscope. For example, a high-resolution video endoscope may be brought into contact with a 2 or 3 CCD system or even a 3D video endoscope. This reduces the design costs and the cost of parts, even in the case of small quantities. By the permitted use of the same parts, which is possible by the option to use different contact technologies or contact assignments with one and the same electrical connection piece, the costs of replacement parts and storage can be reduced in the case of larger quantities.

It is possible, for example when the contacting surfaces are soldered to the stranded wires of a cable, to carry out the soldering when the two arms of the electrical connection piece are not yet superimposed. This also relates to a connection between the contact pins of the image-producing unit and the feedthroughs in the central section of the circuit board. The feedthroughs and the contacting surfaces are exposed so that soldering is able to be undertaken without the potentially obstructively arranged arms. Automated soldering may also take place.

The arms can branch off in opposing directions from the central section and the axis of symmetry can extend at least approximately parallel or perpendicular to a common direction of longitudinal extent of the arms. Depending on the arrangement of the axis of symmetry, after selecting the desired contact technology, the electrical connection piece is rotated about its longitudinal axis or turned transversely thereto. It is also possible to provide a contact assignment which is symmetrical, both parallel and perpendicular, to the direction of longitudinal extent. Thus, the electrical connection piece may be turned or rotated in any manner without faulty contact being possible. The handling is thus particularly simple and the risk of faulty mounting is limited to a minimum.

Moreover, the first contacting surfaces in the first and second end surfaces or the second contacting surfaces in the third and fourth end surfaces can be connected to contacts of a further electrical connecting element, such as one or more cables, one or more flexible circuit boards or one or more plug connectors.

The central section of the circuit board can comprise a first side and an opposing second side. The first side of the central section is arranged with the first electrical contacting surfaces on a common flat side of the circuit board. Accordingly, the second side of the central section is arranged with the second electrical contacting surfaces on a common flat side of the circuit board. Depending on the desired contact technology, with which the further electrical connecting element is intended to be brought into contact, the first or the second flat side of the central section faces the feedthrough of the image-producing unit. Accordingly, the first and second arms are bent, such that the arms are at least indirectly superimposed so that they are located in a half space facing the opposing side of the central section. Before or after the bending process, the contacting surfaces are brought into contact using the desired contact technology.

Moreover, the first and the second contact technology which is different therefrom can be selected from the following list: soldering, plug connection and connecting by corner vias as well as other generally known contact technologies.

The central section and/or the end surfaces and the further end surfaces of the circuit board can be stiffened and/or less flexible than the arms. If the central section of the circuit board is configured to be stiffened or less flexible than the arms, it is possible simply to push the central section onto the contact pins of the hermetically sealed feedthrough and to fix it there. This also simplifies the subsequent soldering of the contact pins. A stiffened or less flexible embodiment of the end surfaces of the arms simplifies the connection to the further electrical connecting element.

The first arm and the second arm can have at least approximately the same length and placed at least partially flat on top of one another, wherein in the superimposed state the first and the second end surfaces or the third and the fourth end surfaces face away from the central section and in the superimposed state together with the central section form a substantially symmetrical triangle, wherein the superimposed end surfaces are placed substantially on a central axis or rotational axis of the image-producing unit.

A distance between the respective free end of the arm and an edge of the central section facing the free end, at which the central section merges with the relevant arm, can be regarded as the length of the arms.

The aforementioned arrangement of the arms relative to the central section, such as, to a central axis or rotational axis of the image-producing unit facilitates an image rotation of the image-producing unit, for example a video unit, at the same time ensuring a more reliable electrical contact. Such an axially symmetrical arrangement does not give preference to either of the two possible twisting directions, for example clockwise or counter-clockwise, so that uniform wear, for example of an adjoining flexible circuit board, is present and neither of the two possible rotational directions is preferred.

According to an embodiment, a flat stabilising body is provided, the stabilising body being arranged between the superimposed end surfaces, wherein the stabilising body can comprise an electrically insulating material and can further comprise a material by means of which signal crosstalk is reduced in the strip conductor portions and/or further strip conductor portions in the end surfaces of the first arm and the second arm.

In the bent-back state of the arms, the stabilising body can be arranged between the respectively superimposed end surfaces. The stabilising body can also be formed from an insulating material. Moreover, the stabilising body can be produced from a material which reduces signal crosstalk.

The stabilising body ensures that secure contact is able to be made with the further electrical connection piece. At the same time, the stabilising body insulates the internal unused contacting surfaces from one another.

According to a further embodiment, a connecting element can be provided, the connecting element penetrating and connecting together the end surfaces, such as being configured as mushroom-shaped projections on both sides of the stabilising body. The connecting element represents a simple, rapidly mountable and efficient retaining function for the two arms on one another. The connecting element may also be a screw connection or a riveted connection. The stabilising body can also be configured to be electrically insulating. Alternatively, the arms can be adhesively bonded on the internal end surfaces to one another or to the stabilising body.

According to a further embodiment, the contact openings of the central section of the circuit board can be plugged via contact pins of the hermetically sealed feedthrough and can be soldered to the contact pins.

The central section of the circuit board does not have to lie flat on a surface of the hermetically sealed feedthrough. Thus, solder is prevented from penetrating the intermediate space which is present, due to a capillary action, and optionally leading to short-circuits between the contact pins.

The object can be further solved by an endoscope, such as a video endoscope, comprising a shaft and a hermetically sealed image-producing unit, such as a video unit, arranged in the shaft, wherein the endoscope further comprises an electrical connection piece according to one or more of the aforementioned embodiments.

The same or similar advantages pertain to the endoscope, as already have been mentioned with regard to the electrical connection piece. Therefore, a further description has been dispensed with.

The object can be still further solved by a method for establishing an electrical connection in an endoscope, wherein an electrical connection piece according to one or more of the aforementioned embodiments is provided, and the first or the second contact technology and/or contact assignment is selected for contacting the electrical connection piece, wherein when the first contact technology and/or contact assignment is selected:
  a first side of the central section, which is arranged with the first electrical contacting surfaces on a common flat side of the circuit board, faces the feedthrough of the image-producing unit and is placed with the contact openings onto the contact pins thereof and soldered,
  the first arm and the second arm are bent toward one another and the third and fourth end surfaces of the arms are superimposed and connected together so that the first electrical contacting surfaces face outwardly,
  subsequently, electrically conductive connections of the first electrical contacting surfaces with electrical conductors of a further electrical connecting element are established according to the first contact technology and/or contact assignment, when the second contact technology and/or contact assignment is selected:
  a second side of the central section, which is arranged with the second electrical contacting surfaces on a common flat side of the circuit board, faces the feedthrough of the image-producing unit and is placed with the contact openings onto the contact pins thereof and soldered,
  the first arm and the second arm are bent toward one another, and the first and second end surfaces of the arms are superimposed and connected together so that the second electrical contacting surfaces face outwardly,
  subsequently, electrically conductive connections of the second electrical contacting surfaces with electrical conductors of a further connecting element are established according to the second contact technology and/or contact assignment.

The first and second arms can be indirectly superimposed.

The method for establishing an electrical connection is able to be implemented efficiently since the choice of contact technology has to be made at a later time during the production process of the endoscope, such as the video endoscope. Therefore, the method is able to be adapted rapidly and flexibly to external boundary conditions. Since the electrical connection piece is able to be used as the same part for a plurality of different types of endoscope or video endoscope the method is able to be implemented particularly economically.

The first and the second contact technology which is different therefrom can be selected from the following list: soldering, plug connection, connection by corner vias and the first and/or second contacting surfaces can be brought into contact by one of these contact technologies.

Moreover, the first arm and the second arm can have at least approximately the same length and are at least partially placed flat on top of one another, wherein the first and the second end surfaces or the third and the fourth end surfaces in the superimposed state face away from the central section and in the superimposed state together with the central section form a substantially symmetrical triangle, wherein in particular the superimposed end surfaces are substantially arranged on a central axis or rotational axis of the image-producing unit.

According to a further embodiment, a flat stabilising body can be arranged between the superimposed end surfaces, wherein the stabilising body can comprise an electrically insulating material and further can comprise a material by means of which signal crosstalk is reduced in the strip conductor portions and/or further strip conductor portions in the end surfaces of the first arm and of the second arm.

Further, the first arm and the second arm can be connected to a connecting element which penetrates the end surfaces, wherein the connecting element can form mushroom-shaped projections on both sides of the stabilising body.

The same or similar advantages also relate to the method, as have been already mentioned with regard to the electrical connection piece, so that repetition is intended to be dispensed with.

BRIEF DESCRIPTION OF THE DRAWINGS

Further features may be derived from the description of embodiments together with the claims and the accompanying drawings. Embodiments may fulfil individual features or a combination of several features.

The embodiments are described hereinafter without limiting the general inventive idea by means of such exemplary embodiments with reference to the drawings, wherein relative to all individual details which are not described in more detail in the text, reference is expressly made to the drawings, in which.

In the drawings, the same or similar elements and/or parts are respectively provided with the same reference numbers, so that a further description in each case is dispensed with.

DETAILED DESCRIPTION

Figure 1:
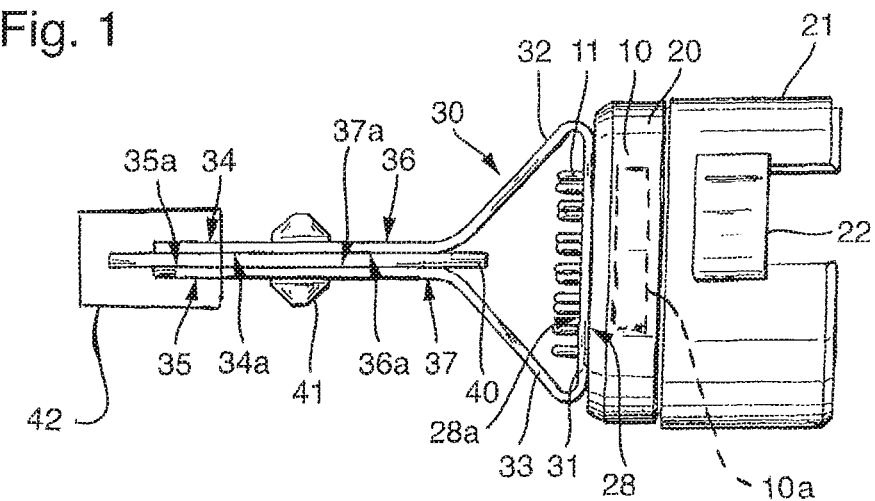
FIG. 1 illustrates a side view of an electrical connection piece which is placed on a feedthrough of an image-producing unit, for example, a video unit or an R-unit.

FIG. 1 illustrates an electrical connection piece for an endoscope, for example a video endoscope, schematically and simplified from the side. On the right-hand image side a hermetically sealed feedthrough 10 of an image-producing unit 10a, for example a video unit or an R-unit, is shown. This feedthrough is arranged in a housing 20, a housing part 21 for receiving a plug connection and a screw connection point 22 being adjoined to the housing part 21 at the proximal end to the right in FIG. 1.

Contact pins 11 protrude from the feedthrough 10 at the distal end of the hermetically sealed feedthrough 10, to the left in FIG. 1. The contact pins 11 also protrude from the hermetically sealed feedthrough 10 on the proximal side, but they are concealed by the housing 20 in perspective. The contact pins 11 are, by way of example, cast in a glass plate so that the feedthrough 10 at this point is hermetically sealed.

A central section 31 of a flexible circuit board 30 is placed onto the distal protruding ends of the contact pins 11. In the central section 31 are located contact openings, not visible in FIG. 1, which in size and arrangement correspond to the contact pins 11 on the hermetically sealed feedthrough 10. The central section 31 of the flexible circuit board 30 can comprise a spacing from the hermetically sealed feedthrough 10 which, however, is selected to be so small that it is not visible in FIG. 1.

The flexible circuit board 30 has a first arm 32 and a second arm 33 which adjoin the central section 31. The first arm 32 and the second arm 33 are configured to be bendable and extend from the central section 31 in different directions to one another, such as in opposing directions. The first arm 32 has at its end facing away from the central section 31 a first flat end surface 36 which can be configured to be stiffened but is at least less flexible than the remaining arm 32. Also, the second arm 33 has at its end facing away from the central section 31 a second flat end surface 37 which, in a similar manner to the first end surface 36, can be configured to be stiffened but is at least less flexible than the second arm 33.

First electrical contacting surfaces 34, 35 are present in the first and second end surfaces 36, 37. Strip conductors (34a, FIG. 4), extend between the contact openings, which enclose the contact pins 11, and the first contacting surfaces 34, 35. Thus, an electrical connection can be provided between the contacting surfaces 34, 35 and the contact pins 11.

Moreover, it is provided that the first arm 32 comprises a flat third end surface 36a opposing the first end surface 36. The second arm 33 comprises a flat fourth end surface 37a opposing the second end surface 37. Second electrical contacting surfaces 34a, 35a are present in the third and fourth end surfaces 36a, 37a. Further strip conductors 43, similar to those shown in FIG. 4 on the first end surface 36), can extend between the second electrical contacting surfaces 34a, 35a and the contact openings, the contact pins 11 being received therein.

In order to achieve the arrangement shown in FIG. 1, the first and the second arms 32, 33 are bent and indirectly superimposed in their end regions. A stabilising body 40 is located between the superimposed portions of the arms 32, 33. In the exemplary embodiment shown, the stabilising body 40 is located between the third end surface 36a and the fourth end surface 37 and is produced from an electrically insulating material. Thus, the internal second contacting surfaces 34a, 35a are electrically insulated from one another. The stabilising body 40 can be produced from a material, by means of which signal crosstalk is reduced in the strip conductor portions and/or further strip conductor portions which extend in the end surfaces 36, 36a, 37, 37a of the first arm 32 and of the second arm 33.

The first electrical contacting surfaces 34, 35 are configured for contacting using a first contact technology. In contrast thereto, the second electrical contacting surfaces 34a, 35a are designed for contacting using a second contact technology which is different therefrom. In the exemplary embodiment shown in FIG. 1, the arms 32, 33 are bent such that the first electrical contacting surfaces 34, 35 are located on the outside, i.e. freely accessible for the contact.

One possible first contact technology is, for example, soldering, a plug connection or even a connection by corner vias. A second contact technology provided for the second contacting surfaces 34a, 35a differs from the first contact technology provided for the first contacting surfaces 34, 35, which can also be selected from the aforementioned list. Depending on which contact technology is provided and/or desired for the electrical connection piece, the arms 32, 33 are optionally bent in the configuration shown in FIG. 1 or in a reverse configuration. This means that the third and fourth end surfaces 36a, 37a (as shown) are superimposed and the first electrical contacting surfaces 34, 35 are freely accessible, or the first and second end surfaces 36, 37 are superimposed and the second electrical contacting surfaces 34a, 35a are accessible for contact. Accordingly, a first side 28 (as shown) or a second side 28a of the central section 31 faces the hermetically sealed feedthrough 10.

After the completed bending procedure, the ends of the arms 32, 33 are connected together by a connecting element 41. This connecting element can be configured such that it forms mushroom-shaped projections on both sides of the arms. According to further exemplary embodiments, not shown, it is also provided to screw together or even to bond together the ends of the arms 32, 33.

Figure 3:
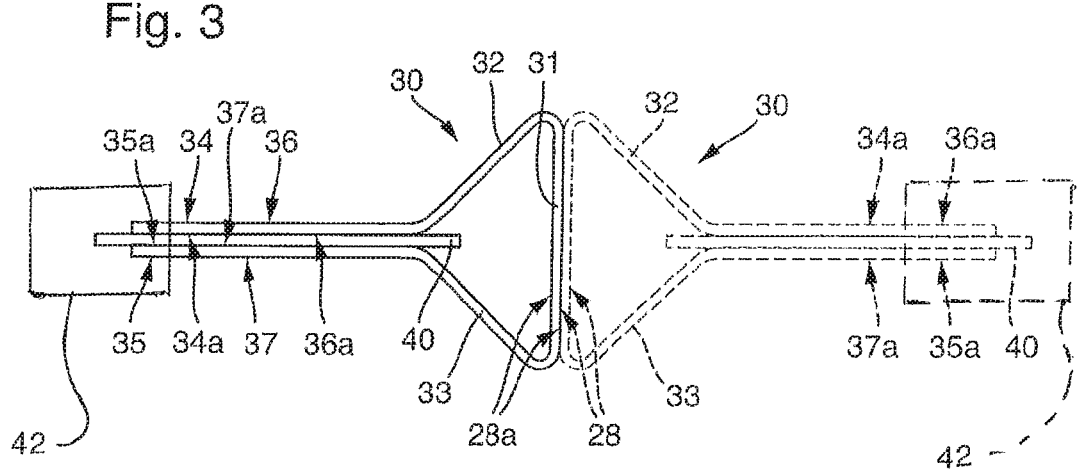
FIG. 3 illustrates a schematically simplified view of the electrical connection piece which illustrates how the two arms are bent or are to be bent in different directions.

The electrical connection piece, after contact and/or connection to the hermetically sealed feedthrough 10, is connected to a further electrical connecting element, such as connector plugs 42 (FIG. 3). To this end, the first contacting surfaces 34, 35 and/or the second contacting surfaces 34a, 35a are brought into contact with the further electrical connecting element. For example, said contacting surfaces are soldered to one or more cable(s) or a flexible circuit board or brought into contact with a plug connector. In this connection, the stiffened and/or less flexible design of the arms 32, 33 in the end regions thereof simplifies the handling.

The electrical connection piece can be provided for use in an endoscope, such as a video endoscope. The image-producing unit 10a is, for example, a video unit or an R-unit which is designed to be rotatable. The contacting surfaces 34, 34a, 35, 35a can be located and/or able to be located substantially on a central axis or rotational axis of the image-producing unit 10a. In order to achieve this, the first arm 32 and the second arm 33 are bent such that, in the superimposed state of the end surfaces, the arms 32, 33 together with the central section 31 form a substantially symmetrical triangle.

Figure 2:
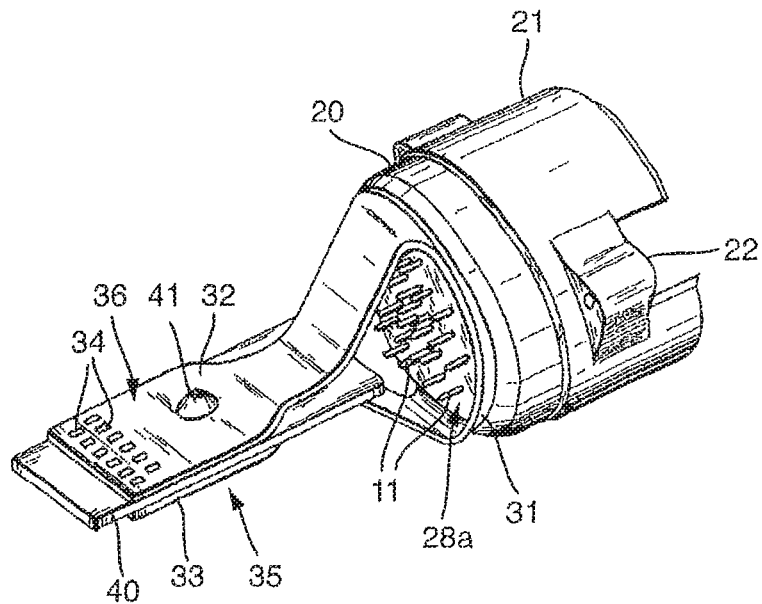
FIG. 2 illustrates a schematically simplified perspective view of the connection piece according to FIG. 1.

FIG. 2 illustrates the arrangement known from FIG. 1 in a simplified schematic and perspective view. By way of example, the first contacting surfaces 34 of the first arm 32 in the first end surface 36 are visible. They are by way of example designed as contacts for a soldered contact or for contact by means of a plug connector.

FIG. 3 illustrates in solid lines a schematic and simplified side view of the circuit board 30, the arms 32, 33 thereof, as shown in FIG. 1, being bent. The first contacting surfaces 34, 35 are located on the outer face of the superimposed portions of the arms 32, 33. The first end surface 36 and the second end surface 37 face outwardly. The connecting element 41 (see FIG. 1) is not shown for reasons of clarity.

In the right-hand part of FIG. 3 the flexible circuit board 30 and the stabilising body 40 are shown in dashed lines, wherein the arms 32, 33 are bent in the reverse direction. In this state, the third end surface 36a and the fourth end surface 37a are located on the outer face so that the second contacting surfaces 34a, 35a are accessible from the outside.

Depending on in which direction the arms 32, 33 are bent, a first side 28 or a second side 28a of the central section 31 is also located on the outer face of the circuit board 30 and in the contacted state faces the hermetically sealed feedthrough 10. In the state shown by the solid line, the first side 28 of the central section 31 is located on the outer face of the circuit board 30, and this circuit board is pushed onto the contact pins 11 such that the first side 28 faces the hermetically sealed feedthrough 10 (see also FIG. 1). In the state shown in dashed lines, the second side 28a of the circuit board 30 is located on the outer face thereof. Now the second contacting surfaces 34a, 35a are intended to be used for being brought into contact with the contact pins 11 of the hermetically sealed feedthrough 10. The flexible circuit board 30 is pushed onto the contact pins 11 such that the second side 28a of the central section 31 faces the hermetically sealed feedthrough 10.

Figure 4:
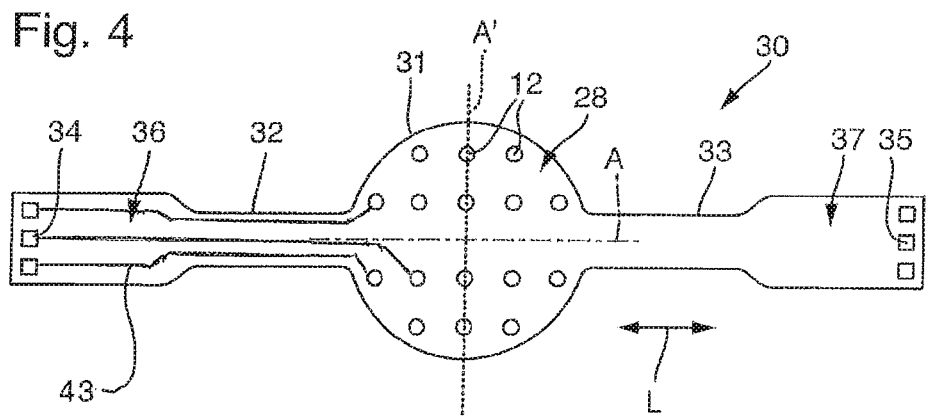
FIG. 4 illustrates a schematically simplified plan view of an electrical connection piece, the arms thereof not being bent but being configured to be flat.

In order optionally to place the first or the second side 28, 28a onto the contact pins 11 of the hermetically sealed feedthrough 10, the circuit board 30 is turned and its arms 32, 33 are correspondingly bent back. In order, however, to permit a corresponding contact of the contact pins 11, without causing faulty contact, a contact assignment of the contact openings 12 provided in the central section 31 is designed to be mirror-symmetrical. This is shown in the schematically simplified plan view of FIG. 4. FIG. 4 shows a side of the circuit board 30, wherein the arms 32, 33 are not bent back. By way of example, the contact openings 12 are designed mirror-symmetrically to the axis of symmetry A shown (shown in dashed-dotted lines), which extends approximately parallel to a common direction of longitudinal extent L of the arms 32, 33. A further axis of symmetry A' (shown in dotted lines) extends at least approximately perpendicular to the direction of longitudinal extent L. In the exemplary embodiment shown, the arrangement of the contacts and the contact assignment thereof are mirror-symmetrical both to the axis of symmetry A and to the further axis of symmetry A'. Thus, it is possible optionally to tilt or to turn the circuit board 30 shown and optionally to place said circuit board onto the contact pins 11 with the first side 28 or the opposing second side 28a and to connect it thereto.

According to an exemplary method for establishing an electrical connection in an endoscope, in particular in a video endoscope, an electrical connection piece as shown in FIGS. 1 to 4 is provided. Also, the choice is made between the first and the second contact technology for bringing the electrical connection piece into contact.

If the first contact technology is selected, for example a soldered connection, the first side 28 of the central section 31, which is arranged with the first electrical contacting surfaces 34, 35 on a common flat side of the circuit board 30, faces the feedthrough 10 of the image-producing unit 10a and with its contact openings 12 is placed on the contact pins thereof 11 and soldered. Subsequently, the first and second arms 32, 33 are bent toward one another such that the third and the fourth end surfaces 36a, 37a of the arms 32, 33 are indirectly superimposed. Subsequently, the arms 32, 33 are connected together. A stabilising body 40 is provided between the end surfaces 36a, 37a. As a result, the first electrical contacting surfaces 34, 35 face outwardly. These contacting surfaces are subsequently brought into electrical contact and/or connected to the electrical conductors of a further electrical connecting element according to the first contact technology. For example, a soldered connection is produced. The first electrical contacting surfaces 34, 35 are accordingly designed for this first contact technology, i.e. for example a soldered connection.

If a second contact technology is selected, for example a connection by corner vias, the second side 28a of the central section 31, which is arranged with the second electrical contacting surfaces 34a, 35a on a common flat side of the circuit board 30, faces the feedthrough 10 of the image-producing unit 10a and is placed with the contact openings 12 on the contact pins 11 thereof and soldered. Subsequently, the first arm 32 and the second arm 33 are bent toward one another such that the first and the second end surfaces 36, 37 of the arms 32, 22 are superimposed at least indirectly. The arms 32, 33 are connected together so that the second electrical contacting surfaces 34a, 35a face outwardly. Subsequently, an electrically conductive connection between the second contacting surfaces 34a, 35a, which for example are configured as corner vias, is produced with the electrical conductors of the further electrical connecting element according to the second contact technology.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMBERS

10 Hermetically sealed feedthrough
11 Contact pins
12 Contact openings
20 Housing
21 Housing part
22 Screw connection point
28 First side
28a Second side
30 Flexible circuit board
31 Central section
32 First arm
33 Second arm
34, 35 First contacting surfaces
34a, 35a Second contacting surfaces
36 First end surface
36a Third end surface
37 Second end surface
37a Fourth end surface
40 Stabilising body
41 Connecting element
A, A' Axis of symmetry
L Direction of longitudinal extent

What is claimed is:

1. An electrical connection piece for an endoscope, the electrical connection piece comprising:
an at least partially flexible circuit board comprising:
a central section which is penetrated by contact openings for contact pins of a hermetically sealed feedthrough of an image-producing unit of the endoscope, the contact openings being arranged mirror-symmetrically relative to an axis of symmetry;
a bendable first arm and a bendable second arm, each of the first arm and the second arm extend in different directions from the central section, wherein the first arm having an end facing away from the central section, the end of the first arm comprising a first end surface and the second arm having an end facing away from the central section, the end of the second arm comprising a second end surface, the end of the first arm comprising a third end surface opposing the first end surface and end of the second arm comprising a fourth end surface opposing the second end surface;
first strip conductors extending between the contact openings and first electrical contacting surfaces on the first and second end surfaces; and
second strip conductors extending between the contact openings and second electrical contacting surfaces on the third and fourth end surfaces;
wherein the first electrical contacting surfaces have a first configuration for contacting using one or more of a first contact technology and a first contact assignment and the second electrical contacting surfaces have a second configuration for contacting using one or more of a second contact technology and a second contact assignment, the one or more of the first contact technology and the first contact assignment being different from the one or more of the second contact technology and the second contact assignment.

2. The electrical connection piece according to claim 1, wherein the first and second arms branch off in opposing directions from the central section, and the axis of symmetry extends at least approximately parallel or perpendicular to a common direction of longitudinal extent of the first and second arms.

3. The electrical connection piece according to claim 1, wherein one of the first contacting surfaces or the second contacting surfaces are connected to contacts of a further electrical connecting element.

4. The electrical connection piece according to claim 3, wherein the first and the second contact technology are selected from a group consisting of soldering, plug connection and connection by corner vias.

5. The electrical connection piece according to claim 1, wherein one or more of the central section, the first and second end surfaces and the third and fourth end surfaces of the circuit board have a rigidity that is less flexible than the first and second arms.

6. The electrical connection piece according to claim 1, wherein the first arm and the second arm have at least approximately the same length and placed flat on top of one another for at least a portion of their length, wherein one of the first and the second end surfaces or the third and the fourth end surfaces face away from the central section and together with the central section form a substantially symmetrical triangle and the first and second end surfaces or third and fourth end surface are placed substantially on a central axis or rotational axis of the image-producing unit.

7. The electrical connection piece according to claim 6, further comprising a stabilising body arranged between one of the first and the second end surfaces or the third and the fourth end surfaces.

8. The electrical connection piece according to claim 7, wherein the stabilising body comprises an electrically insulating material.

9. The electrical connection piece according to claim 7, wherein the electrically insulating material comprises a material by means of which signal crosstalk is reduced in one of the first and second strip conductors.

10. The electrical connection piece according to claim 1, further comprising a connecting element, the connecting element penetrating and connecting together the first and second arms.

11. The electrical connection piece according to claim 10, wherein the connecting element having mushroom-shaped projections on each of two sides of the first and second arms.

12. The electrical connection piece according to claim 1, further comprising a hermetically sealed feed through having contact pins corresponding to the contact openings of the central section, wherein the contact openings are plugged by the contact pins of the hermetically sealed feedthrough.

13. The electrical connection piece according to claim 12, wherein the contact openings are soldered to the contact pins.

14. A method for establishing an electrical connection in an endoscope, wherein an electrical connection piece is provided according to claim 1, the method comprising:
    selecting the one or more of the first contact technology and the first contact assignment or the one or more of the second contact technology and the second contact assignment for contacting the electrical connection piece, wherein
    when the one or more of the first contact technology and the first contact assignment is selected:
    facing a first side of the central section to the feedthrough of the image-producing unit with the contact pins of the feedthrough extending through the contact openings;
    soldering the contact pins to the openings;
    bending the first arm and the second arm toward one another such that the third and fourth end surfaces face each other and are connected together and the first electrical contacting surfaces face outwardly,
    subsequent to the bending, establishing electrically conductive connections of the first electrical contacting surfaces with electrical conductors of a first further electrical connecting element according to the one or more of the first contact technology and the first contact assignment,
    when the one or more of the second contact technology and the second contact assignment is selected:
    facing a second side of the central section to the feedthrough of the image-producing unit with the contact pins of the feedthrough extending through the contact openings;
    soldering the contact pins to the openings;
    bending the first arm and the second arm toward one another such that the first and second end surfaces face each other and are connected together and the second electrical contacting surfaces face outwardly,
    subsequent to the bending, establishing electrically conductive connections of the second electrical contacting surfaces with electrical conductors of a second further electrical connecting element according to the one or more of the second contact technology and the second contact assignment.

15. The method according to claim 14, wherein the first contact technology and the second contact technology are selected from a group consisting of soldering, plug connection and connection by corner vias.

16. The method according to claim 14, wherein the first arm and the second arm have at least approximately the same length and are at least partially placed on top of one another, wherein the first and the second end surfaces or the third and the fourth end surfaces face away from the central section and form a substantially symmetrical triangle.

17. The method according to claim 16, wherein the first and second end surfaces or third and fourth end surface are substantially arranged on a central axis or rotational axis of the image-producing unit.

18. The method according to claim 14, wherein the electrical connection piece further comprises a stabilising body arranged between one of the first and second end surfaces and third and fourth end surfaces;
    wherein the stabilising body comprises an electrically insulating material; and
    the electrically insulating material comprises a material by means of which signal crosstalk is reduced in the first and second strip conductors.

19. The method according to claim 14, wherein the electrical connection piece further comprises a connecting element for connecting the first arm and the second arm), the connecting element penetrating the first and second arms.

20. The method according to claim 19, wherein the connecting element comprises mushroom-shaped projections on each of two sides of the first and second arms.

* * * * *